US008129539B2

(12) United States Patent
Renga et al.

(10) Patent No.: US 8,129,539 B2
(45) Date of Patent: Mar. 6, 2012

(54) PROCESS FOR THE PREPARATION OF 2-SUBSTITUTED-5-(1-ALKYLTHIO)-ALKYLPYRIDINES

(75) Inventors: James M. Renga, Indianapolis, IN (US); Ronald Ross, Jr., Zionsville, IN (US); Timothy P. Martin, Noblesville, IN (US); Kim E. Arndt, Carmel, IN (US); Nicholas M. Irvine, Westfield, IN (US)

(73) Assignee: Dow Agro Sciences LLC, Indianapolis, IN (US)

( * ) Notice: Subject to any disclaimer, the term of this patent is extended or adjusted under 35 U.S.C. 154(b) by 217 days.

(21) Appl. No.: 12/722,978

(22) Filed: Mar. 12, 2010

(65) Prior Publication Data

US 2010/0168436 A1    Jul. 1, 2010

Related U.S. Application Data

(62) Division of application No. 12/392,644, filed on Feb. 25, 2009, which is a division of application No. 11/704,825, filed on Feb. 9, 2007, now Pat. No. 7,541,469.

(60) Provisional application No. 60/835,940, filed on Aug. 7, 2006.

(51) Int. Cl.
    *C07D 213/00* (2006.01)

(52) U.S. Cl. .................................................... 546/339
(58) Field of Classification Search .................... 546/339
    See application file for complete search history.

(56) References Cited

U.S. PATENT DOCUMENTS

| 7,511,149 | B2 | 3/2009 | Arndt et al. |
| 7,541,469 | B2 | 6/2009 | Renga et al. |
| 7,604,815 | B2 | 10/2009 | Loso et al. |
| 7,678,920 | B2 | 3/2010 | Zhu et al. |
| 7,709,650 | B2 * | 5/2010 | Renga et al. .................. 546/339 |
| 2007/0203191 | A1 | 8/2007 | Loso et al. |
| 2007/0299264 | A1 | 12/2007 | Huang et al. |
| 2008/0108665 | A1 | 5/2008 | Huang et al. |
| 2008/0108666 | A1 | 5/2008 | Loso et al. |
| 2008/0108667 | A1 | 5/2008 | Zhu et al. |
| 2008/0132705 | A1 | 6/2008 | Heller et al. |
| 2008/0194830 | A1 | 8/2008 | Meyer et al. |

FOREIGN PATENT DOCUMENTS

WO    WO2008/018917    2/2008

* cited by examiner

*Primary Examiner* — Nizal Chandrakumar
(74) *Attorney, Agent, or Firm* — Carl D. Corrin; Craig Mixan

(57) ABSTRACT

2-Substituted-5-(1-alkylthio)alkylpyridines are produced efficiently and in high yield from a non-pyridine source by cyclization.

2 Claims, No Drawings

PROCESS FOR THE PREPARATION OF 2-SUBSTITUTED-5-(1-ALKYLTHIO)-ALKYLPYRIDINES

This application is a divisional of U.S. non-provisional application Ser. No. 12/392,644 filed on 25 Feb. 2009, which is a divisional of Ser. No. 11/704,825 filed on 9 Feb. 2007, which claims priority from U.S. provisional application 60/835,940 filed on 7 Aug. 2006. The disclosures of application Ser. Nos. 12/392,644, 11/704,825 and 60/835,940 are hereby incorporated, in their entirety, by reference.

BACKGROUND OF THE INVENTION

The present invention concerns certain novel 2-substituted-5-(1-alkylthio)alkylpyridines and a process for their preparation.

The new 2-substituted-5-(1-alkylthio)alkylpyridines are useful intermediates for the preparation of certain new insecticides; see, for example, U.S. Patent Publication 2005/0228027. It would be advantageous to produce 2-substituted-5-(1-alkylthio)alkylpyridines efficiently and in high yield from a non-pyridine source.

SUMMARY OF THE INVENTION

The present invention concerns 2-substituted-5-(1-alkylthio)alkyl-pyridines and their preparation of by cyclization. More particularly, the present invention concerns a process for the preparation of a 2-substituted-5-(1-alkylthio)alkylpyridine (I),

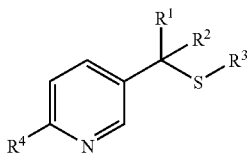
(I)

wherein $R^1$ and $R^2$ independently represent H, $C_1$-$C_4$ alkyl, or either of $R^1$ or $R^2$ taken together with $R^3$ represent a 4- to 6-membered saturated ring, or $R^1$ taken together with $R^2$ represents a 3- to 6-membered saturated ring optionally substituted with an O or a N atom; and $R^3$ represents $C_1$-$C_4$ alkyl or $R^3$ taken together with either of $R^1$ or $R^2$ represent a 4- to 6-membered saturated ring; and $R^4$ represents $C_1$-$C_4$ alkyl or $C_1$-$C_4$ haloalkyl;

which comprises cyclizing an α,β-unsaturated ketone II

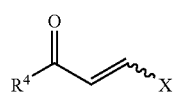
II wherein

X represents halogen, $OR^5 OSO_2R^5$, $SR^5$, $SOR^5$, $SO_2R^5$ or $NR^6R^7$;

$R^5$ represent hydrogen, $C_1$-$C_8$ alkyl, $C_2$-$C_8$ alkenyl, $C_1$-$C_8$ arylalkyl, $C_1$-$C_8$ haloalkyl, $C_1$-$C_8$ alkoxyalkyl, $C_1$-$C_8$ alkylaminoalkyl, aryl or heteroaryl; and $R^6$ and $R^7$ independently represent hydrogen, $C_1$-$C_8$ alkyl, $C_2$-$C_8$ alkenyl, $C_1$-$C_8$ arylalkyl, $C_1$-$C_8$ haloalkyl, $C_1$-$C_8$ alkoxyalkyl, $C_1$-$C_8$ alkylaminoalkyl, aryl or heteroaryl or $R^6$ and $R^7$ taken together with N represent a 5- or 6-membered saturated or unsaturated ring; and $R^4$ is as previously defined;

with an enamine III

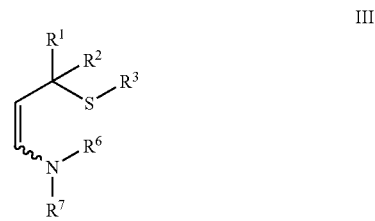
III wherein $R^1$, $R^2$, $R^3$, $R^6$, $R^7$ are as previously defined;

in the presence of ammonia or a reagent capable of generating ammonia.

Another aspect of the invention is the novel compounds having the formula

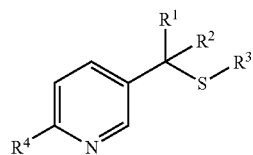

wherein $R^1$ and $R^2$ independently represent H, $C_1$-$C_4$ alkyl, or either of $R^1$ or $R^2$ taken together with $R^3$ represent a 4- to 6-membered saturated ring, or $R^1$ taken together with $R^2$ represents a 3- to 6-membered saturated ring optionally substituted with an O or a N atom; and $R^3$ represents $C_1$-$C_4$ alkyl or $R^3$ taken together with either of $R^1$ or $R^2$ represent a 4- to 6-membered saturated ring; and $R^4$ represents $C_1$-$C_4$ alkyl or $C_1$-$C_4$ haloalkyl, preferably $C_1$-$C_4$ haloalkyl.

DETAILED DESCRIPTION OF THE INVENTION

Unless specifically limited otherwise, the term "alkyl" (including derivative terms such as "haloalkyl" and "arylalkyl"), as used herein, include straight chain, branched chain, and cyclic groups. Thus, typical alkyl groups are methyl, ethyl, 1-methylethyl, propyl, 1,1-dimethylethyl, and cyclopropyl. The term "alkenyl", as used herein, includes straight chain, branched chain, and cyclic groups and is intended to include one or more unsaturated bonds. The term "halogen" includes fluorine, chlorine, bromine and iodine. The term "haloalkyl" includes alkyl groups substituted with from one to the maximum possible number of halogen atoms. The term "aryl", as well as derivative terms such as "arylalkyl", refers to a phenyl or naphthyl group. The term "heteroaryl" refers to a 5- or 6-membered aromatic ring containing one or more heteroatoms, viz., N, O or S; these heteroaromatic rings may be fused to other aromatic systems.

In the present invention, a 2-substituted-5-(1-alkylthio) alkylpyridine (I),

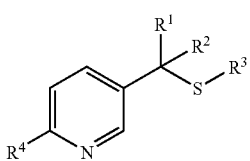

wherein

R¹ and R² independently represent H, $C_1$-$C_4$ alkyl, or either of R¹ or R² taken together with R³ represent a 4- to 6-membered saturated ring, or R¹ taken together with R² represents a 3- to 6-membered saturated ring optionally substituted with an O or a N atom; and R³ represents $C_1$-$C_4$ alkyl or R³ taken together with either of R¹ or R² represent a 4- to 6-membered saturated ring; and R⁴ represents $C_1$-$C_4$ alkyl or $C_1$-$C_4$ haloalkyl is prepared by cyclizing an α,β-unsaturated ketone II

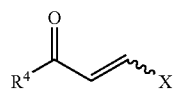

wherein

X represents halogen, $OR^5 OSO_2R^5$, $SR^5$, $SOR^5$, $SO_2R^5$ or $NR^6R^7$;

R⁵ represent hydrogen, $C_1$-$C_8$ alkyl, $C_2$-$C_8$ alkenyl, $C_1$-$C_8$ arylalkyl, $C_1$-$C_8$ haloalkyl, $C_1$-$C_8$ alkoxyalkyl, $C_1$-$C_8$ alkylaminoalkyl, aryl or heteroaryl; and R⁶ and R⁷ independently represent hydrogen, $C_1$-$C_8$ alkyl, $C_2$-$C_8$ alkenyl, $C_1$-$C_8$ arylalkyl, $C_1$-$C_8$ haloalkyl, $C_1$-$C_8$ alkoxyalkyl, $C_1$-$C_8$ alkylaminoalkyl, aryl or heteroaryl or R⁶ and R⁷ taken together with N represent a 5- or 6-membered saturated or unsaturated ring; and R⁴ is as previously defined
with an enamine III

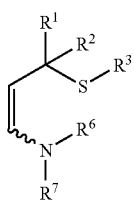

wherein

R¹, R², R³, R⁶, R⁷ are as previously defined.

α,β-Unsaturated ketones (II) are commercially available or can be prepared from the corresponding vinylogous substrates and acylating agents. Typically, alkylvinyl ethers can be acylated with haloalkylacetic anhydrides to yield compounds of type II. Enamines (III) can be conveniently prepared from the addition of a suitably substituted amine to the appropriately substituted aldehyde in the presence of a water adsorbing material, with or without a suitable solvent. Typically, the appropriate substituted 3-alkylthiopropionaldehyde is reacted with an anhydrous disubstituted amine at about −20° C. to about 20° C. in the presence of a desiccant such as anhydrous potassium carbonate, and the product is isolated by distillation.

Approximately equimolar quantities of the α,β-unsaturated ketone (II) and the enamine (III) and ammonia are required in the process, although 2-4 fold excesses of the ammonia or the ammonia precursor are often preferred.

Typical reagents capable of generating ammonia include, for example, 1) an ammonium salt of an acid, preferably an organic acid, 2) formamide, or 3) formamide with an acid or acid salt. The ammonium salt of any aliphatic or aromatic organic acid can be used, but for convenience of processing, the ammonium salts of $C_1$-$C_4$ alkanoic acids are preferred. Ammonium formate and ammonium acetate are most preferred.

This reaction is preferably conducted in a polar high-boiling solvent that is miscible with water. Preferred solvents include amides such as formamide, dimethyl formamide, dimethyl acetamide, alcohols such as methanol, ethanol, isopropanol, (2-methoxy)ethanol and alkylnitriles, with acetonitrile being particularly preferred.

The reaction is conducted at a temperature from about −20° C. to about 150° C. Temperatures from about 0° C. to about 80° C. are usually preferred.

The product is isolated by conventional techniques such as silica gel chromatography or fractional distillation.

In a typical reaction, the α,β-unsaturated ketone (II) and enamine (III) are dissolved in the polar solvent at about −5° C. to about 20° C. and agitated until the α,β-unsaturated ketone (II) and enamine (III) are consumed. The ammonium salt of the organic acid is then added, and the mixture is heated until the reaction is complete. After dissolving in a non water miscible solvent and washing with water and, optionally, brine, the 2-substituted-5-(1-alkylthio)alkylpyridine (I) is isolated by vacuum distillation.

The following examples are presented to illustrate the invention.

EXAMPLES

Example 1

Preparation of
5-(1-Methylthio)ethyl-2-(trifluoromethyl)pyridine

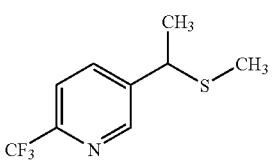

Step 1. Preparation of
1-(3-Methylthiobut-1-enyl)pyrrolidine

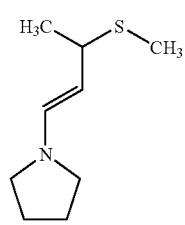

To a dry 5000 milliliter (ml) round bottom flask equipped with mechanical stirrer, nitrogen inlet, addition funnel, and thermometer, was charged 591 g (4.27 moles) of dry granular potassium carbonate and 1428 ml (17.1 moles) of anhydrous pyrrolidine. The mixture was stirred under a atmosphere of nitrogen, and cooled to 4° C. with an ice bath, after which 1050 ml (8.9 moles) of 3-methyl-thiobutyraldehyde was added at a rate that maintains the temperature below 10° C. Upon the completion of the addition, the cooling bath was removed and the reaction was allowed to reach room temperature. The reaction contents were then filtered through a sintered glass filter funnel to remove the solids and the solids were washed with 200 ml of anhydrous ethyl ether. The filtrate was concentrated under vacuum on a rotary evaporator until all of the pyrrolidine was removed to afford 1,519 g of 1-(3-methylthiobut-1-enyl)pyrrolidine as a red liquid. $^1$H NMR CDCl$_3$ δ 1.36 (d, 3H), 1.85 (m, 4H), 2.02 (s, 3H), 3.02 (m, 4H), 3.26 (q, 1H), 3.98 (dd, 1H), 6.25 (d, 1H).

Step 2. Preparation of
5-(1-Methylthio)ethyl-2-(trifluoromethyl)pyridine

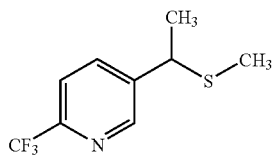

To a dry 5000 ml round bottom flask equipped with mechanical stirrer, nitrogen inlet, addition funnel, and thermometer, was charged 654 ml (4.59 moles) of 4-ethoxy-1,1,1-trifluoro-but-3-en-2-one and 1000 ml of anhydrous acetonitrile. The solution was cooled to 5° C. and 786 g (4.59 moles) of 1-(3-methylthiobut-1-enyl)pyrrolidine was added at a rate which maintains the temperature below 10° C. After the addition was complete, the cooling bath was removed. The reaction was stirred at room temperature for 1.5 hours and 530 g (6.88 moles) of ammonium acetate was then added in one portion, and the reaction was heated at 80° C. for 1.5 hours. Upon cooling, the reaction was concentrated under vacuum on a rotary evaporator to remove the acetonitrile, and the residue was dissolved in 3 liters of ethyl ether. The ether extract was washed with 3×100 ml of water to remove the ammonium acetate, dried over anhydrous magnesium sulfate, filtered, and concentrated under vacuum on a rotary evaporator. The crude product was purified by Kugelrohr distillation at 0.3 mm Hg. The material that distills at 85-110° C. was collected to afford 599 g of the title compound, 5-(1-methylthio)ethyl-2-(trifluoromethyl)pyridine as a yellow oil. $^1$H NMR CDCl$_3$ δ 1.62 (d, 3H), 1.95 (s, 3H), 3.93 (q, 1H), 7.67 (d, 1H), 7.90 (dd, 1H), 8.67 (d, 1H)

Example 2

Preparation of
5-(1-Methylthio)ethyl-2-(trifluoromethyl)pyridine

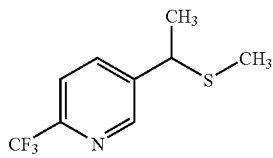

Step 1. Preparation of
N,N-Dimethyl-(3-methylthiobut-1-enyl)amine

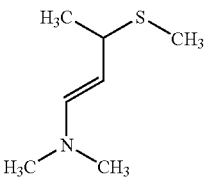

To a dry 50 ml round bottom flask equipped with a magnetic stirrer was added 3-methylthiobutyraldehyde (2.04 g, 17.2 mmol), potassium carbonate (1.19 g, 8.6 mmol), and anhydrous acetonitrile (5 ml). The flask was fitted with a 3-way stopcock and the air was evacuated under house vacuum. Dimethylamine (excess) was introduced into the system via a balloon attached to the stopcock, and the resulting magnetically stirred suspension was placed in a water bath to moderate the fairly significant exotherm. The balloon was recharged with dimethylamine and the reaction was stirred at room temperature for 90 minutes, at which time GC analysis of an aliquot indicated full consumption of the aldehyde starting material. The reaction was filtered and the solvent removed on the rotary evaporator to give the crude N,N-dimethyl-(3-methylthio-but-1-enyl)amine as a light yellow liquid (2.45 g). $^1$H NMR CDCl$_3$ δ 1.35 (d, 3H), 2.00 (s, 3H), 2.60 (s, 6H), 3.24 (m, 1H), 4.06 (dd, 1H), 5.97 (dd, 1H).

Step 2. Preparation of
5-(1-Methylthio)ethyl-2-(trifluoromethyl)pyridine

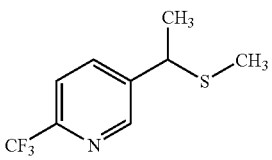

The N,N-dimethyl-(3-methylthiobut-1-enyl)amine (2.45 g, 17.0 mmol) was dissolved in anhydrous acetonitrile (10 ml) and 4-ethoxy-1,1,1-trifluorobut-3-en-2-one (2.90 g, 17.2 mmol) was added dropwise at room temperature over a ten minute period, and the light-orange solution was stirred at room temperature for 16 hours. To the resulting burgundy solution was added ammonium acetate (1.33 g, 17.2 mmol), and the reaction was warmed to reflux and stirred for 1 hour. The reaction was cooled to room temperature, diluted with diethyl ether (150 ml), washed with water (3×50 ml), washed with brine (50 ml), dried over sodium sulfate, filtered, and the solvent removed in vacuuo on the rotary evaporator. The resulting brown liquid was purified via flash chromatography (SiO$_2$, 20% EtOAc/hexanes) to give 5-(1-methylthio)ethyl-2-(trifluoromethyl)pyridine as an orange liquid (1.67 g, 44%). $^1$H NMR CDCl$_3$ δ 1.62 (d, 3H), 1.95 (s, 3H), 3.93 (q, 1H), 7.67 (d, 1H), 7.90 (dd, 1H), 8.67 (d, 1H).

What is claimed is:
1. A compound of the formula

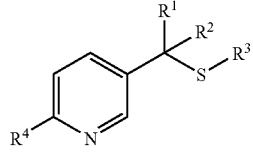

wherein
R$^1$ and R$^2$ independently represent H, C$_1$-C$_4$ alkyl, or either of R$^1$ or R$^2$ taken together with R$^3$ represent a 4- to 6-membered saturated ring, or R$^1$ taken together with R$^2$ represents a 3- to 6-membered saturated ring optionally substituted with an O or a N atom; and $R^3$ represents $C_1$-$C_4$ alkyl or $R^3$ taken together with either of $R^1$ or $R^2$ represent a 4- to 6-membered saturated ring; and $R^4$ represents $C_1$-$C_4$ alkyl or $C_1$-$C_4$ haloalkyl.

2. The compound of claim 1 in which $R^1$ and $R^2$ independently represent H or methyl, $R^3$ represents methyl and $R^4$ represents trifluoromethyl.

* * * * *